(12) United States Patent
Kambara et al.

(10) Patent No.: US 8,765,474 B2
(45) Date of Patent: Jul. 1, 2014

(54) AUTOMATIC ANALYZER AND THE ANALYZING METHOD USING THE SAME

(75) Inventors: Katsuhiro Kambara, Hitachinaka (JP);
Shigenori Watari, Hitachinaka (JP);
Hidetoshi Sugiyama, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 862 days.

(21) Appl. No.: 12/032,339

(22) Filed: Feb. 15, 2008

(65) Prior Publication Data
US 2008/0213903 A1 Sep. 4, 2008

(30) Foreign Application Priority Data
Feb. 19, 2007 (JP) .................................. 2007-037309

(51) Int. Cl.
*G01N 35/02* (2006.01)
(52) U.S. Cl.
USPC ............... 436/50; 436/43; 436/180; 422/500; 422/501; 422/502; 422/503
(58) Field of Classification Search
USPC ........................ 422/500–503; 436/43, 50, 180
See application file for complete search history.

(56) References Cited

U.S. PATENT DOCUMENTS

| 4,815,978 | A | * | 3/1989 | Mazza et al. ...................... 435/4 |
| 4,871,682 | A | * | 10/1989 | Mazza ........................... 436/179 |
| 5,646,046 | A | * | 7/1997 | Fischer et al. ................... 422/63 |
| 6,812,032 | B1 | | 11/2004 | Carver, Jr. et al. |
| 2003/0198125 | A1 | | 10/2003 | Linsen et al. |
| 2004/0034479 | A1 | | 2/2004 | Shimase et al. |
| 2004/0219062 | A1 | * | 11/2004 | Platano et al. ................... 422/63 |
| 2005/0221370 | A1 | | 10/2005 | Hodge |
| 2005/0237521 | A1 | | 10/2005 | Hirono |

FOREIGN PATENT DOCUMENTS

| DE | 19907448 A1 | 8/2000 |
| JP | 2003-035715 | 2/2003 |
| WO | 9638730 A1 | 12/1999 |
| WO | 2006/121997 A2 | 11/2006 |

* cited by examiner

*Primary Examiner* — Jyoti Nagpaul
(74) *Attorney, Agent, or Firm* — Mattingly & Malur, PC

(57) ABSTRACT

An automatic analyzer which assures uniformity in mixing effects regardless of sample quantity and test item and thus produces analysis results with high repeatability. The automatic analyzer includes a device for adding a conditioning liquid into a reaction chamber so that the quantity of liquid in the reaction chamber becomes a predetermined quantity prior to being mixed. The conditioning liquid may be a diluent or physiological saline as used for dilution of a sample or any other special liquid that adjusts the properties such as viscosity, surface tension, etc. of liquid to be mixed.

7 Claims, 4 Drawing Sheets

FIG. 3

| TEST ITEM | CONDITIONING LIQUID TYPE |
|---|---|
| Test Item A | Conditioning Liquid α |
| Test Item B | Conditioning Liquid β |
| Test Item C | Conditioning Liquid α |
| ⋮ | ⋮ |

FIG. 4

| TEST ITEM | QTY OF SAMPLE | QTY OF REAGENT | QTY OF CONDITIONING LIQUID |
|---|---|---|---|
| Test Item A | Qty AA | Qty aa | Target Qty V−(Qty AA + Qty aa) |
| Test Item B | Qty BB | Qty bb | Target Qty V−(Qty BB + Qty bb) |
| ⋮ | ⋮ | ⋮ | ⋮ |

AUTOMATIC ANALYZER AND THE ANALYZING METHOD USING THE SAME

CLAIM OF PRIORITY

The present application claims priority from Japanese application serial No. 2007-37309 filed on Feb. 19, 2007, the content of which is hereby incorporated by reference into this application.

BACKGROUND OF THE INVENTION

1. Field of the Invention

The present invention relates to an automatic analyzer and automatic analyzing method which carries out qualitative and quantitative analyses of biological or chemical samples such as blood and urine and more particularly to an automatic analyzer with a mixing device.

2. Description of the Related Art

It is known that conventional chemical or biochemical analyzers use a reaction liquid obtained by mixing a sample such as a serum with a desired reagent as an object of analysis and further measure its absorbance. This kind of analyzer is comprised of a mechanism for providing a sample and a reagent into a reaction chamber or cuvette, a mechanism for mixing a sample and a reagent in a reaction chamber, a mechanism for analyzing physical properties of a sample which is reacting or has finished reaction, and so on.

A major technical problem in analyzers is reduction of the required quantities of sample and reagent for analysis. One reason for this is that as the number of test items increases, the quantity of sample available for one test item decreases. For example, in blood tests of infants, the quantity of blood sample available for analysis is very small. In addition, from the viewpoint of cost, there is a demand for the reduction in the quantity of reagent used in analysis. This is due to the growing tendency that advanced analysis techniques are introduced and expensive reagents are widely used.

As the quantities of sample and reagent used for analysis were decreased, the size of reaction chambers were reduced accordingly. However, this has led to a new problem. For example, when the reaction liquid is mixed mechanically by a spatula or the like, the ratio of reaction liquid taken out or the ratio of rinse fluid taken in becomes larger, which affects the analysis result. One solution to this problem related to mixing is a non-contact mixing device using ultrasonic waves as described in JP-A No. 2003-35715. However, in this case, for the sample and reagent which are injected into a reaction chamber, their mixture ratio varies depending on the type of test, or test item. So the quantity of liquid to be measured in the chamber is different and complicated control work is needed for accomplishing efficient mixing.

The technique described in JP-A No. 2003-35715 uses a plurality of ultrasonic oscillators provided at different heights so that mixing efficiency does not deteriorate even when the liquid level of liquid to be mixed varies. In this case, complicated control work is needed to determine which oscillator should be activated according to the liquid level. Also it is desirable to adjust the oscillation intensity depending on the properties of the liquid to be mixed (viscosity, etc). Not only in non-contact ultrasonic mixing but also in mechanical mixing with a spatula, a smaller quantity of liquid to be mixed makes it more difficult to ensure uniformity in mixing.

An object of the present invention is to provide an automatic analyzer and analyzing method having a mixing device with a simple structure which is able to mix liquids uniformly regardless of the quantity of sample present and liquid properties thereof.

SUMMARY OF THE INVENTION

In order to achieve the above object, the present invention provides an automatic analyzer as summarized below.

The automatic analyzer includes a liquid adding device for adding a conditioning liquid into a reaction chamber, wherein the predetermined quantity of liquid is prepared in each reaction chamber before the mixing.

The reaction chamber is a container in which a sample and a reagent are mixed to react with each other. The reaction liquid in the reaction chamber is analyzed qualitatively and quantitatively by an optical method (measurement of change in absorbance, etc). For the mixing device, various mixing methods are available. For example, a spatula is moved for mixing or the outside of the reaction chamber is irradiated with ultrasonic waves to agitate the liquid by acoustic radiation pressure. The conditioning liquid may be a diluent or physiological saline as used for dilution of a sample or any other special liquid that adjusts the properties of liquid to be mixed (viscosity, surface tension, etc). In automatic analyzers, the quantity of reagent is several times as much as the quantity of sample and the properties of liquid to be mixed largely depends on those of the reagent. Therefore, the properties of the conditioning liquid are optimized depending on those of the reagent and the properties of liquid to be mixed become almost identical regardless of the test item.

Therefore, according to the present invention, there is provided an automatic analyzer which assures uniformity in mixing effects regardless of the sample quantity and test item and thus produces analysis results with high repeatability.

BRIEF DESCRIPTION OF THE DRAWINGS

The invention will be more particularly described with reference to the accompanying drawings, in which:

FIG. 3 shows an example of a table according to an embodiment of the present invention; and FIG. 4 shows an explanatory table of a method of determining the quantity of conditioning liquid according to an embodiment of the present invention.

DETAILED DESCRIPTION OF THE PREFERRED EMBODIMENT

Next, a preferred embodiment of the present invention will be described referring to the accompanying drawings.

Figure 1:
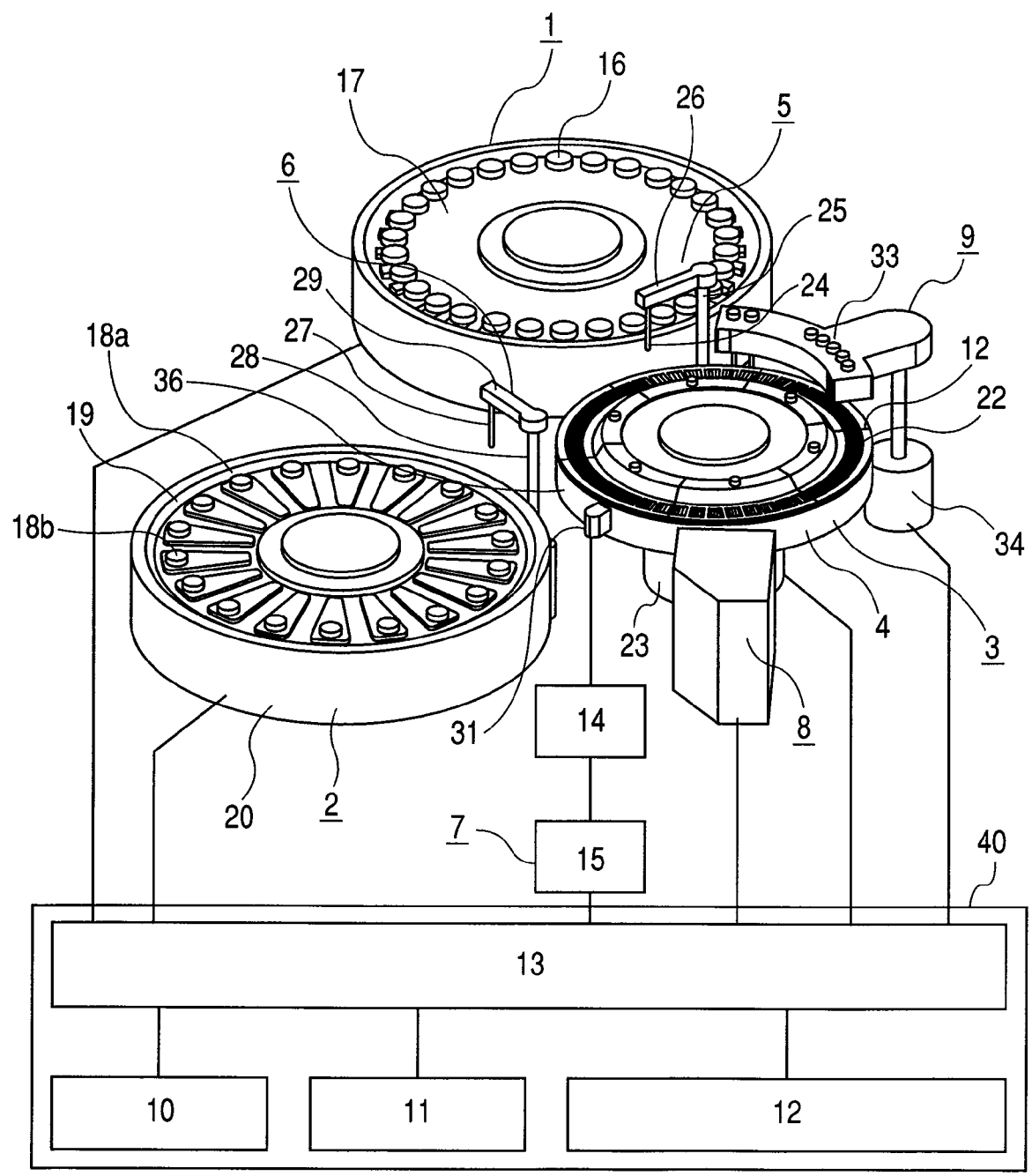
FIG. 1 is a perspective schematic diagram of an automatic analyzer according to an embodiment of the present invention.
Figure 2:
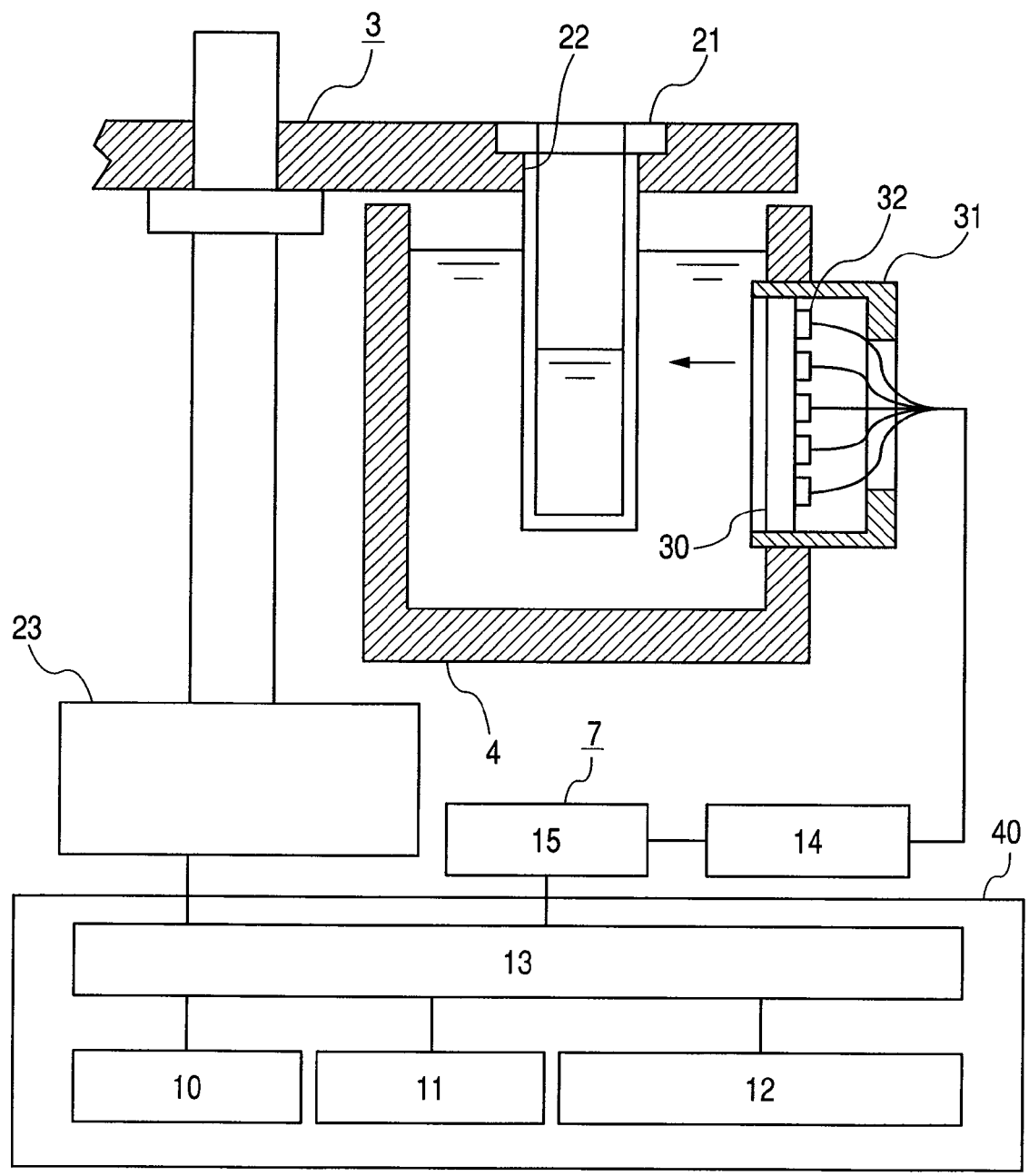
FIG. 2 is a schematic diagram of a mixing mechanism provided in the automatic analyzer and its vicinity according to an embodiment of the present invention.

FIG. 1 is a perspective schematic diagram showing the structure of an automatic analyzer according to an embodiment of the invention and FIG. 2 is a schematic diagram showing a longitudinal sectional view of a mixing mechanism provided in the automatic analyzer and its vicinity.

The automatic analyzer according to this embodiment is mainly composed of a sample disk 1, a reagent disk 2, a reaction disk 3, a reaction bath 4, a sampling mechanism 5, a pipetting mechanism 6, a mixing mechanism 7, a photometric mechanism 8, a rinsing mechanism 9, and a controller 40. The controller 40 further includes a display unit 10, an input unit 11, a memory 12, and a control unit 13.

Referring to FIG. 1, in the sample disk 1, plural sample containers 16 containing collected samples are arranged and fixed on the circumference of a circular disk 17 which is rotated in the circumferential direction in a way that it can be repositioned by a drive mechanism composed of a motor, a rotary shaft and so on (not shown).

In the reagent disk 2, plural reagent bottles 18a, which contain reagents to be mixed with samples for reaction, and conditioning liquid bottles 18b are arranged and fixed on the circumference of a circular disk 19 which is surrounded by a temperature-controlled cold storage 20. The circular disk 19 is rotated in the circumferential direction in a way that it can be repositioned by an ordinary drive mechanism composed of a motor, a rotary shaft and so on (not shown).

The reaction disk 3, equipped with plural reaction chamber holders 22 provided as a hole in the reaction disk 3 which hold reaction chambers 21 for samples and reagents, is circumferentially rotated and stopped repeatedly in a cycle by a drive mechanism 23 to transport the reaction chambers 21 intermittently.

The reaction bath 4 is provided along the length of movement of the reaction chambers 21. The reaction bath 4 serves as an incubation bath which uses, for example, a temperature-controlled liquid to control the reaction liquid in a reaction chamber 21 to a given temperature in order to accelerate chemical or biochemical reaction between the sample and reagent. The reaction chambers 21 move inside the reaction bath 4.

The sampling mechanism 5 includes a probe 24, an arm 26 fitted to a support shaft 25 and a drive mechanism (not shown). The drive mechanism is provided for the movement of the probe 24 between the sample disk 1 and the reaction disk 3 with the support shaft 25 as the center of rotation. According to a predetermined sequence, the sampling mechanism 5 supplies a sample in a sample container 16 transported to a predetermined position by rotation of the sample disk 1, to a reaction chamber 21.

Similarly, the pipetting mechanism 6 includes a probe 27, an arm 29 fitted to a support shaft 28 and a drive mechanism (not shown). The drive mechanism enables the movement of the probe 27 between the reagent disk 2 and the reaction disk 3 with the support shaft 28 which operates as the center of rotation. According to a predetermined sequence, the pipetting mechanism 6 supplies a reagent in a reagent bottle 18a or a conditioning liquid in a conditioning liquid bottle 18b to a reaction chamber 21. The reagent bottle 18a or conditioning liquid bottle 18b is transported to a predetermined position by the rotation of the reagent disk 2. The sample containers 16 and reagent bottles 18a contain different types of samples and reagents respectively and as much sample and reagent as needed are supplied to a reaction chamber 21. Likewise, the conditioning liquid bottles 18b contain different types of conditioning liquids and as much conditioning liquid as needed is supplied to the reaction chamber 21.

Referring to FIG. 1, the mixing mechanism 7 is a non-contact mixing mechanism which irradiates the reaction chamber 21 transported to it (mixing position) with sonic waves sideways to mix the sample, reagent and conditioning liquid in the reaction chamber 21. It includes a vibrating part 31 fixed in a position to permit the reaction chamber 21 in the mixing position to be irradiated with sonic waves sideways, a piezoelectric element driver 14 for driving a piezoelectric element 30 and a mixing mechanism controller 15. The mixing mechanism controller 15, which is connected with the control unit 13, drives the piezoelectric element driver 14.

As shown in FIG. 2, in the mixing mechanism 7, the piezoelectric element 30 as a sound source is provided to the vibrating part 31 with one side of it immersed in temperature-controlled water. The piezoelectric element 30 includes a plurality of electrodes 32 which are driven at a given frequency by the piezoelectric element driver 14. The irradiated direction of the sonic waves are controlled by selecting from amongst the electrodes 32 those which are to be driven.

Referring to FIG. 2, a reaction chamber 21 including a sample and a reagent in it is fixed in the reaction disk 3 through a reaction chamber holder 22. As the reaction disk 3 rotates in the circumferential direction, the reaction chamber 21 moves along immersed in the reaction bath 4 with temperature-controlled water in it.

Then, as it arrives at the mixing position and stops, at least one of the piezoelectric elements 30, which depend on the quantity and properties of the liquid for reaction, is oscillated at a prescribed frequency by the piezoelectric element driver 14. Oscillating waves generated by the oscillated piezoelectric elements 30 are transmitted as sonic waves through the temperature-controlled water of the reaction bath 4 and reach the sample and reagent in the reaction chamber 21. The transmitted oscillating waves cause swirls, which stimulate movement of the sample and mix the sample and the reagent.

Referring to FIG. 1, the photometric mechanism 8 measures properties of the sample in a photometrically (measurement of absorbance of the reaction liquid in the reaction chamber 21, etc). The rinsing mechanism 9 includes a plurality of nozzles 33 and a mechanism 34 for moving them up and down. It sucks the reaction liquid in the reaction chamber 21 and discharges the rinse fluid to rinse the chamber 21 transported to it (rinsing position).

Again referring to the controller 40 of FIG. 1, the display unit 10 shows test items, test results and so on as various screen displays and the input unit 11 is used to enter test items and other information. The memory 12 stores predetermined sequences (programs) for controlling various mechanisms and other information (test items, etc).

The automatic analyzer according to this embodiment further includes a syringe and a pump as components and all these components are controlled by the control unit 13.

The operation of the automatic analyzer will be described next.

First, the reaction chamber 21 rinsed by the rinsing mechanism 9 is transported to the sample injection position by rotation of the reaction disk 3. Then, a sample container 16 with a sample in it is transported to the sampling position by rotation of the sample disk 1. Similarly the reagent disk 2 transports a required reagent bottle 18a to the pipetting position.

Then, the sampling mechanism 5 is activated to inject a sample from the sample container 16 transported to the sampling position into the reaction chamber 21 transported to the sample injection position using the probe 24. The reaction chamber 21 with the injected sample in it is transported to the reagent injection position and a reagent is injected from the sample bottle 18a transported to the pipetting position on the reagent disk 2, into the reaction chamber 21 transported to the reagent injection position, by the pipetting mechanism 6.

Then, the reaction chamber 21 is transported to the conditioning liquid injection position. Meanwhile, the reagent disk 2 transports a required conditioning liquid bottle 18b to the pipetting position and as the reaction chamber 21 arrives at the conditioning liquid injection position, a conditioning liquid is injected from the conditioning liquid bottle 18b into the reaction chamber 21 transported to the conditioning liquid injection position, by the pipetting mechanism 6.

The reaction chamber 21, which now contains the injected sample, reagent and conditioning liquid, is transported to the mixing position where they are mixed by the mixing mechanism 7.

The absorbance of the reaction liquid thus mixed is measured by the photometric mechanism 8 while the reaction chamber 21 is passing between the light source and the photometer. This measurement cycle is made several times and after finishing all measurement cycles, the reaction chamber 21 is rinsed by the rinsing mechanism 9.

A series of steps as mentioned above are taken for each reaction chamber 21 so that the automatic analyzer makes analysis according to this embodiment.

The characteristics of this embodiment will be explained below.

This embodiment is characterized in that a conditioning liquid is injected in addition to the sample and reagent before the reaction chamber 21 arrives at the mixing position and thus the quantity and properties of liquid for reaction are controlled within prescribed ranges.

For the above characteristics, the analyzer takes the following preparations under the control of the control unit 13:

(1) To determine the type of conditioning liquid; and
(2) To determine the injection quantity of the conditioning liquid.

The first preparation is made, for example, by entering of the type of conditioning liquid suitable for each test item as a parameter through the input unit 11. Alternatively, it is also possible that a look-up table of conditioning liquid types suitable for different test items as shown in FIG. 3 is saved in the memory 12 in advance and for each test, the type of conditioning liquid is determined by referring to the look-up table. Another alternative approach is that barcode information is provided with each reagent. The barcode includes information on the type of conditioning liquid suitable for the reagent. And upon entry of the reagent, information on the type of conditioning liquid is also read from the barcode and saved in the memory 12 so that the type of conditioning liquid is determined automatically.

Figure 5:
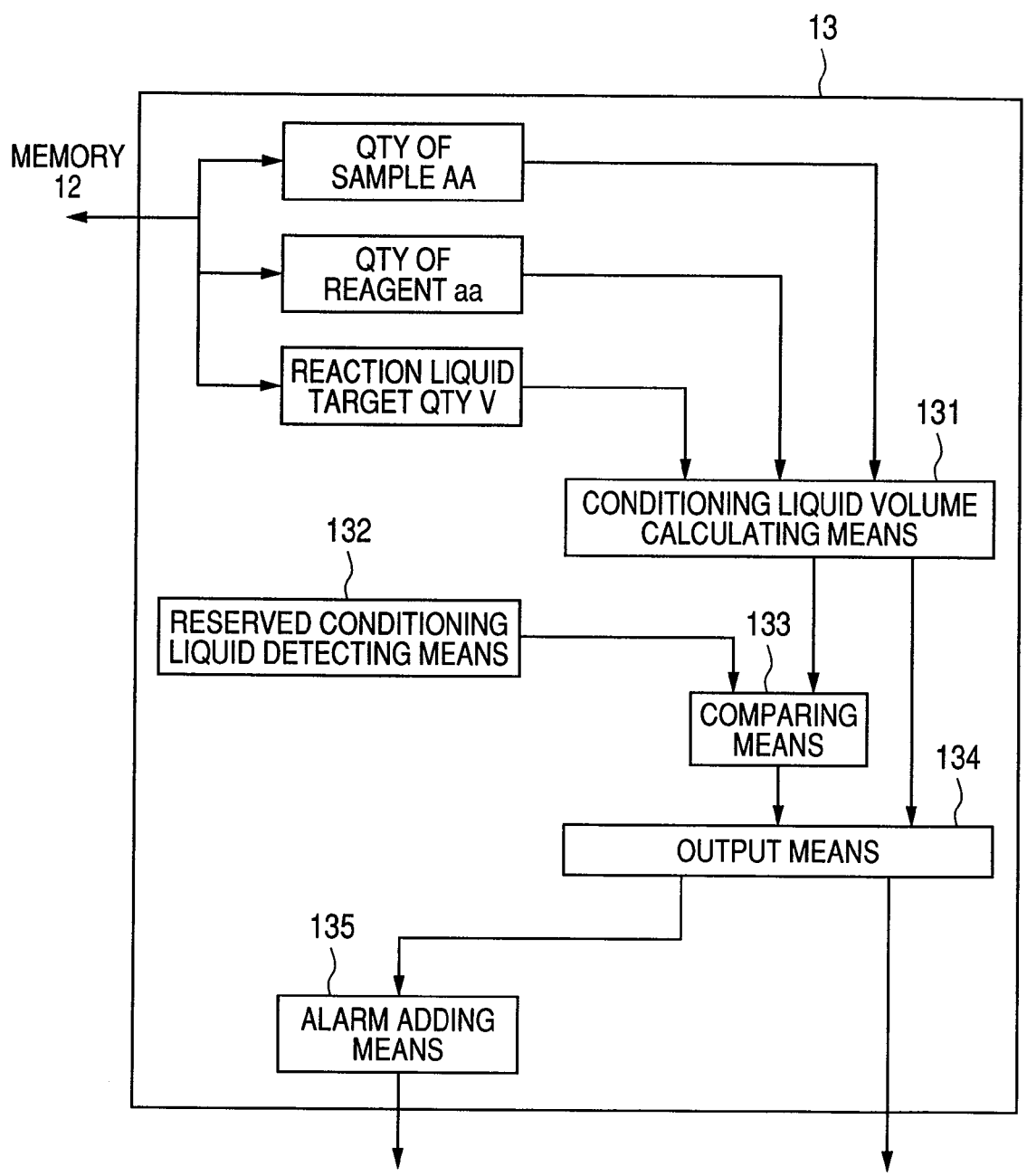
FIG. 5 is a block diagram showing the composition of the control unit 13.

For the second preparation, the injection quantity is determined, for example, by subtracting the sum of the quantities of sample and reagent from the target quantity of liquid as shown in FIG. 4. Then, the composition of the control unit 13 in the controller 40 is described in FIG. 5. According to the requested analyzing item, a needed volume of sample, reagent and target volume of reaction liquid are extracted from the look-up table shown in FIG. 4. and input in the control unit 13. The look-up table is stored in the memory 12 in the controller 40.

In the control unit 13, an output of the conditioning liquid volume calculating means 131 and the output of a reserved conditioning liquid detecting means 132 are compared in a comparing means 132 and the result is input to output means 134. Then, the output means sends a analyzing start command to the analyzer when the volume of the reserved conditioning liquid in the bottle 18b satisfies the needed volume. When the volume of the reserved conditioning liquid is less than the needed volume, the output means 134 sends an analyzing inhibiting command to the analyzer.

When the volume of reserved conditioning liquid is less than needed after the analysis has started, an alarm adding means 135 adds alarm information to the analyzing result.

These processes are performed by the sequence program processed in the control unit 13. Further, a special hard logic circuit may also be utilized instead.

Properties of the liquid for reaction such as viscosity and wettability are controlled within ranges suitable for solution mixing by injection of a conditioning liquid.

After the above two preparations are made, finally the conditioning liquid is injected in the reaction cuvette 21 to adjust the quantity and properties of liquid for reaction so that the required quantities of sample and reagent can be decreased without extremely reducing the size of the reaction chamber 21.

In other words, the required quantities of sample and reagent can be decreased without the possibility of encountering a new technical problem which might arise from a reaction chamber size reduction.

In addition, since the quantity and properties of the liquid for reaction are controlled within prescribed ranges, the mixing mechanism 7 can be simplified.

In other words, the need for complicated control work involved in dealing with different liquid quantities and properties for different test items is eliminated and also the number of electrodes 32 can be decreased, which means that the mixing mechanism 7 can be simplified.

What is claimed is:

1. An automatic analyzer provided with a reaction chamber in which a quantity of a sample and a quantity of a predetermined reagent according to a test item which indicates a type of test are provided, and a controller configured to control an automatic analyzing process of the reaction chamber, the automatic analyzer comprising:

a pipetting mechanism providing the predetermined reagent and a particular conditioning liquid to the reaction chamber;

a photometric mechanism measuring properties of the sample by measurement of absorbance of a reaction liquid including the sample, the predetermined reagent and the particular conditioning liquid, a memory storing the quantity of the sample and the quantity of the predetermined reagent provided to the reaction chamber according to each test item and a predetermined target quantity of liquid in the reaction chamber, and wherein the controller is further configured to determine the particular conditioning liquid from amongst a plurality of different conditioning liquids corresponding to a plurality of test items and to control the pipetting mechanism to provide the determined particular conditioning liquid to the reaction chamber to control the properties of the reaction liquid within prescribed ranges in each test item in a quantity which is determined by subtracting the sum of the quantities of sample and reagent from the predetermined target quantity of liquid, which is predetermined commonly for the plural test items.

2. The automatic analyzer according to claim 1, wherein plural types of the conditioning liquid are prepared in the automatic analyzer and a predetermined type of conditioning liquid for each of a plurality of test items is selected by the controller and added to the reaction chamber.

3. The automatic analyzer according to claim 1, wherein the controller is configured to receive entry of conditioning liquid information simultaneously with entry of the test item to the controller.

4. The automatic analyzer according to claim 1, wherein the particular conditioning liquid is specified with reference to a look-up table provided in the controller and the content of the look-up table is associated with the test item and a plurality of other test items.

5. The automatic analyzer according to claim 1, wherein corresponding conditioning liquid information is recorded on a reagent bottle used for the test item and the predetermined conditioning liquid is specified according to the information.

6. The automatic analyzer according to claim 1, wherein the controller is further configured to determine the particular conditioning liquid from amongst the plurality of different conditioning liquids corresponding to the plurality of test items and to control the pipetting mechanism to provide the determined particular conditioning liquid to the reaction chamber to control the properties of the reaction liquid within prescribed ranges in each test item such that the properties of the reaction liquid become almost identical regardless of the test item.

7. The automatic analyzer according to claim 1, wherein the controller is further configured to determine the particular conditioning liquid from amongst the plurality of different conditioning liquids corresponding to the plurality of test items and to control the pipetting mechanism to provide the determined particular conditioning liquid to the reaction chamber to control the properties of the reaction liquid within prescribed ranges in each test item such that the viscosity of the reaction liquid becomes almost identical regardless of the test item.

* * * * *